United States Patent [19]

Hyman et al.

[11] Patent Number: 5,384,240
[45] Date of Patent: Jan. 24, 1995

[54] BASE DISSOCIATION ASSAY

[75] Inventor: Jones M. Hyman, Durham, N.C.

[73] Assignee: Akzo Nobel, N.V., Arnhem, Netherlands

[21] Appl. No.: 981,689

[22] Filed: Nov. 25, 1992

[51] Int. Cl.⁶ ............................................. C12Q 1/70
[52] U.S. Cl. .................................... 435/5; 435/7.1; 435/7.92; 435/7.93; 435/7.94; 435/7.95; 435/974; 436/820; 436/825; 436/826
[58] Field of Search .................. 435/5, 7.1, 7.92–7.95, 435/974; 436/820, 825, 826

[56] References Cited

U.S. PATENT DOCUMENTS

| | | | |
|---|---|---|---|
| 4,299,812 | 11/1981 | Coombes | 424/1 |
| 4,459,359 | 7/1984 | Neurath | 436/507 |
| 5,047,325 | 9/1991 | Pronovost et al. | 435/7.36 |
| 5,081,010 | 1/1992 | Cummins et al. | 435/5 |
| 5,124,245 | 6/1992 | Cummins et al. | 435/5 |
| 5,132,205 | 7/1992 | Pronovost et al. | 435/5 |
| 5,210,039 | 5/1993 | Cummins et al. | 436/17 |

Primary Examiner—Christine M. Nucker
Assistant Examiner—Jeffrey Stucker
Attorney, Agent, or Firm—William M. Blackstone; Mary E. Gormley

[57] ABSTRACT

This invention relates to a novel reagent and a method of using the reagent in an immunoassay to detect antigens, particularly antigens immunocomplexed with their corresponding or cross-reacting antibodies. In particular, this reagent and method increase the detection of human immunodeficiency virus HIV-1 p24 core antigen.

12 Claims, 9 Drawing Sheets

BASE DISSOCIATION ASSAY

DESCRIPTION OF THE INVENTION

This invention relates to a novel reagent and a method of using the reagent in an immunoassay to detect antigens, particularly antigens immunocomplexed with their corresponding or cross-reacting antibodies. In particular, this reagent and method increase the detection of human immunodeficiency virus HIV-1 p24 core antigen.

BACKGROUND OF THE INVENTION

Biological samples, usually serum or plasma, but also urine, cerebral spinal fluid or other bodily fluids, containing immunologically active antigens often also contain quantities of antibodies that react with these antigens. These antibodies will bind to the antigens present and form immunocomplexes. These immunocomplexes may prevent detection of the antigens by tying up the binding sites present on the antigens. This poses a particular problem when a sample is being tested with an immunoassay for the presence of such antigen. Generally, the immunoassay will contain an antibody that is specific for the antigen in question, and will therefore need to have access to the binding sites on the antigen in order to capture or form an immunocomplex with it. If all of the binding sites on the antigen are complexed with antibodies present in the sample, no capture of the antigen will occur in the immunoassay, and the antigen will not be detected.

This problem has been seen in particular with the detection of the p24 core antigen of the human immunodeficiency virus, HIV-1.

In order to detect infection by HIV-1, to check on the progress of the disease it causes, acquired immunodeficiency syndrome (AIDS), or to monitor therapy, detecting the p24 core antigen of HIV-1 is highly desirable. However, available assays for the detection of HIV-1 p24 antigenemia in serum or plasma are able to detect HIV infection only before seroconversion of antibody from negative to positive occurs. Once antibodies to HIV begin to appear, these tests are severely limited in their ability to detect antigen. It is generally thought that these limitations are caused by the presence of anti-p24 antibodies in the blood that complex with the antigen, thereby blocking the reactive sites that would otherwise be available to complex with the antibodies of the test immunoassays. T. M. McHugh et al. discussed this issue in "Relation of Circulating Levels of Human Immunodeficiency Virus (HIV) Antigen, Antibody to p24, and HIV-Containing Immune Complexes in HIV-Infected Patients," J. Inf. Dis., 158, no. 5, pages 1088-1091, November 1988.

At least two solutions have been proposed to deal with this problem. Both solutions attempt to dissociate the immunocomplexes formed in the sample while still maintaining the viability of the antigen and at the same time prevent the newly dissociated antibody from recombining with the antigen.

The currently preferred solution is that of subjecting the serum or plasma sample to an acid dissociation treatment prior to testing it in an immunoassay (P. Nishanian et al., "A Simple Method for Improved Assay Demonstrates that HIV p24 Antigen is Present as Immune Complexes in Most Sera from HIV-Infected Individuals," J. Inf. Dis., 162, pages 21-28, July, 1990; R. C. Bollinger, Jr. et al., "Acid Dissociation Increases the Sensitivity of p24 Antigen Detection for the Evaluation of Antiviral Therapy and Disease Progression in Asymptomatic HIV-Infected Persons," J. Inf. Dis., 165, pages 913-916, May, 1992; S. Kontio, "Sensitive One-Step Enzyme Immunoassay for HIV-1 p24 Antigen in Human Blood Specimens and Cell Culture Supernatants," J. Imm. Methods, 139, pages 257-263, 1991). Generally, the method involves taking the serum or plasma, mixing it with an acid such as 0.5N HCl (pH from about 2.0 to 3.0), incubating for 60 to 90 minutes at 37° C., and neutralizing with a base such as 0.5N NaOH (pH from about 6.8 to 7.2). The sample so prepared is then used in the immunoassay of choice.

This method relies on the supposition that under acidic conditions antibodies are irreversibly inactivated more readily than many antigens. Antigen detection in the presence of antibody has been shown to be enhanced substantially by this method, but there are several drawbacks.

The first is that antigens as well as antibodies are inactivated in this method, as demonstrated by some laboratory procedures where although the test samples are acid pretreated, the standards containing only p24 are not. It is easy to see that when the antigens are also affected during treatment, the sensitivity needed to detect antigen in low antigen containing and/or non-antibody containing samples is reduced.

Another drawback is that the test sample must be pretreated prior to its being tested in an immunoassay. This involves an additional step of handling the test sample in order to do the immunoassay, increasing the chances of infection of laboratory personnel. Exposure of laboratory personnel to possibly infectious samples increases as the number of steps to perform the immunoassay increases, as does the possibility for error when transferring the contents of one microtiter plate well to another.

Acid treatment may cause precipitation or clotting of biological samples, thereby interfering with later assay procedures. Because of this problem, the samples must be diluted, usually three fold, to reduce the effects of the precipitation or clotting. However, when a sample having only a small amount of antigen is diluted, the chances of detecting the antigen decrease.

Another method proposed to dissociate the immunocomplex while leaving the antigen intact and available for further testing is the method of S. A. Fiscus et al., using a polyethylene glycol precipitation method (S. A. Fiscus et al., "Detection of Infectious Immune Complexes in Human Immunodeficiency Virus Type 1 (HIV-1) Infections: Correlation with Plasma Viremia and CD4 Cell Counts," J. Inf. Dis., 164, pages 765-769, October 1991). This method is a complex one where the test plasma is specially filtered, mixed with polyethylene glycol (PEG-8000), vortexed, refrigerated overnight, centrifuged, and the pellets washed twice in 2% PEG. The supernatants and aliquots of the PEG precipitates can then be tested in an immunoassay that detects p24. This method appears to have detected p24 in samples containing anti-p24 antibody or p24 immunocomplexes, but it is not currently used as a standard method to detect the presence of p24. Among other drawbacks, it is an involved procedure with multiple steps necessitating much handling of the test specimen and long incubation periods.

What is needed is a method for detecting the presence of antigen that has been immunocomplexed with antibody in a test sample, in particular, p24 complexed with anti-p24 antibodies in a sample. Additionally, such method should be done with a minimum amount of steps, so as to reduce the exposure of the laboratory personnel handling potentially infected samples.

SUMMARY OF THE INVENTION

The present invention is a method used to treat samples that may contain antigens bound in an antigen-antibody immunocomplex, in order to make the antigens available for detection in an immunoassay. In particular, the present method is suitable in testing by immunoassay for HIV-1 p24 antigen in samples, both in the presence or absence of anti-p24 antibodies, and whether or not immunocomplexes have formed with the p24. The method comprises mixing the sample with a high pH solution or buffer, thereby raising the pH to about 8.0 or greater, and then assaying the treated sample with the appropriate immunoassay to detect the presence or absence of the antigen. The dissociation step may be carried out either before or during the immunoassay procedure, without any need to neutralize the sample prior to immunoassay.

Another embodiment of the invention is the dissociation reagent, a solution or composition with a pH about or greater than 8.0 consisting primarily of surfactant, salt and buffer with a pKa at a basic pH.

DESCRIPTION OF PREFERRED EMBODIMENTS

Figure 1:
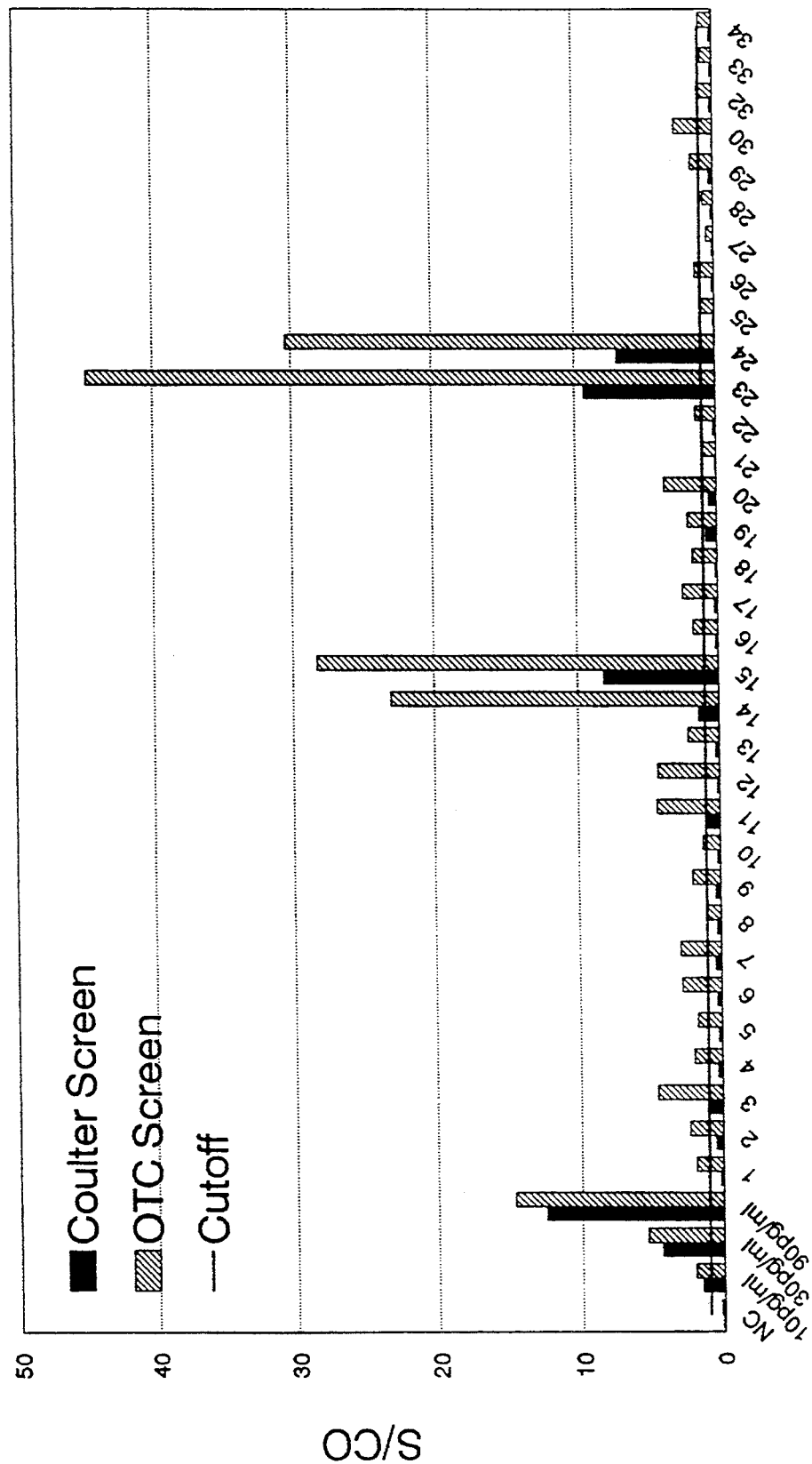
FIG. 1 is a graph of samples tested for HIV-1 p24 antigen using the Coulter Corporation screening immunoassay and the Organon Teknika Corporation screening immunoassay showing the samples tested versus their calculated S/CO ratio.

The present invention is a base dissociation method used to treat samples that may contain antigens bound in an antigen-antibody immunocomplex in order to dissociate the antigens and make them available for detection in an immunoassay. It has also been seen to improve detection of non-complexed antigen when incubated overnight, in comparison to acid pretreated samples. In particular, this method is less damaging to antigens than is the currently preferred acid dissociation method, and is therefore able to increase the immunoassay's ability to detect small amounts of antigen in the sample.

During or prior to the immunoassay, the sample is treated by this method to dissociate immunocomplexes and to release immunologically active antigen. The dissociation step involves adding an aliquot of the sample to be tested to an aliquot of a base, a high pH solution or buffer ("solution") and incubating the mixture for a specified time period. After incubation, the sample is ready to be used in an immunoassay. As this treatment step may be done in the immunoassay apparatus, such as a microtiter well that already contains the reagents needed to begin the immunoassay, the immunoassay can then proceed. If the sample treatment occurs in another container, the sample can then be transferred to the test vehicle, such as a microtiter well, to begin the immunoassay.

Antigens include peptides, proteins, haptens, nucleic acids or other antibody binding analytes. Examples of some antigens include HIV antigens, such as HIV-1 p24 antigen, HIV-2 p24 antigen, HTLV-I and HTLV-II antigens and antigens from Hepatitis C Virus.

Antibodies are either monoclonal or polyclonal, and are reactive with the antigens of interest in the sample. Although polyclonal antibodies are those found in biological samples, it is possible to use monoclonal antibodies under controlled test conditions. The inventive method will dissociate these antibodies from the antigens of interest, minimizing the damage inflicted on the antigens, thereby allowing them to be detected in an immunoassay.

The high pH solution used in this method includes bases such as sodium hydroxide and potassium hydroxide or buffers with a pKa at basic pH, such as phosphates, amines and zwitterionics. Preferably, a solution such as a dissociation reagent, containing a buffer, detergents or surfactants, salts and/or animal serum is used. The detergents are nonionics, anionics, cationics and zwitterionics, such as Tween 20 (a polyoxyethylene sorbitan monolaurate, sold by Sigma Chemical Co., St. Louis, Mo. USA), Nonylphenol 40 (ethoxylated nonylphenol, also sold by Sigma Chemical Co.), and sodium dodecyl sulfate. Sera from animals, such as bovine or horse, may also be used. In addition, various preservatives, antimicrobials, and salts, well-known to those skilled in the art of developing solutions, needed to produce a stable solution are included in this type of solution. A preferred composition consists of ethanolamine at a range from about 0.01M to about 10.0M, Triton ® X-100 (a phenoxypolyethyoxyethanol, a registered trademark off Rohm and Haas, Philadelphia, Pa. USA) at a range from 0 to about 10% and NaCl at a range from 0% to about 3M. The most preferred solution consists of 2M ethanolamine, Triton ® X-100 at a concentration of 2.5%, and 0.15M NaCl. This solution is used at a ratio of one part solution to approximately four parts test sample.

The solution has a pH in the range of about 8.0 to about 14, with a preferred range being from about 10 to 12. At these pH ranges, the solution damages proteins to a much smaller extent than does the acid used in acid dissociation systems. Because of this, neutralization of the mixture of sample and solution is not needed. Therefore, in situ dissociation of immune complexes proceeds during the immunoassay procedure. At high pH, the strength of the antigen-antibody bond is reduced, thus increasing the free:blocked ratio of antigen in the sample. The efficacy of the process relies, not on the destruction of the interfering fluid phase antibody, but on the ability of high affinity solid phase capture antibody, typically used in immunoassays, to outcompete the interfering antibody for binding sites on the antigen.

Once the sample and the solution have been mixed, the immunoassay may proceed. Immunoassay includes any assay where reaction occurs between antibody and antigen, no matter the format, be it competitive, sandwich, inhibition, or other formats not currently known. Generally, the antibody of the immunoassay is bound to a solid substrate, such as microtiter plate wells, cellulose strips, beads, the inner surface of test tubes or capillary tubes, and particles such as gold sol, red blood cells, and latex particles.

The following examples are given to further describe the invention.

EXAMPLE 1

Comparison of Coulter and OTC Immunoassays

This experiment was performed to compare the Coulter Corporation screening assay, Coulter ™ HIV p24 Ag Assay and Organon Teknika Corporation's (OTC) Vironostika® HIV-1 Antigen Microelisa System screening assay for the presence of HIV-1 p24 in samples.

The same samples were used in both assays. Thirty-three serum samples all known to contain some level of antibody to p24 antigen, a negative control and three standards were tested. The three standards are normal serum samples spiked with commercially available Dupont HIV-1 lysate, at levels of 10, 30 and 90 pg p24/ml of serum.

The Coulter assay was performed according to the manufacturers' directions, as described below.

200 µl of controls, standards and samples were transferred to wells in a microtiter plate that was previously coated by the manufacturer with a p24 antibody. 20 µl of Lyse Buffer was added to each well, the plate covered and incubated at 37° C. for one hour. The cover was then removed and the solution aspirated. 300 µl of Wash Buffer was used to wash the wells six times, and after the final washing, the liquid was removed. Next, 200 µl of CH-Biotin working solution was added to each well and the plates were covered and allowed to incubate at 37° C. for one hour. The solution was discarded and 200 µl of SA-HRPO (horseradish peroxidase) was added to the wells, which were covered and incubated at 37° C. for 30 minutes. The solution was discarded and the wells were washed six times. 200 µl of TMB substrate solution was added, and the plates were incubated at 30 minutes at room temperature. Finally, 50 µl of CSR-1 (a stop reagent) was added to each well and the plates were read at 450 nm.

The OTC immunoassay was performed as follows.

25 µl of Disruption Buffer (4M urea and 1% saponin, 2.0% normal horse serum, 0.2% gentamicin sulfate, 0.005% cinnamaldehyde, 0.01% amaranth, FD&C red dye no. 2 as coloring agent, 0.02% ethanol, 0.15M NaCl and 0.01M sodium phosphate) was added to each anti-p24 antibody coated microtiter well, followed by 100 µl of sample, control or standard. The microtiter plates were then covered and incubated at 37° C. for one hour. Each well was washed four times with diluted Tween 20 and phosphate buffered saline. 100 µl of conjugate (horseradish peroxidase-labeled anti-HIV-1) was added to each well. The microtiter plates were covered and incubated at 37° C. for sixty minutes. Then each well was washed four times with diluted phosphate buffer. Next, 100 µl of substrate (tetramethylbenzidine-2HCl) was added to each well and the plates were incubated at room temperature for 30 minutes. The reaction was stopped by adding 100 µl of the stop solution containing 2N sulfuric acid. The absorbance of the solution in each well was read at 450 nm and the results are shown in FIG. 1. The y-axis is the Signal to Cut-Off ratio (S/CO), which is the optical density read/calculated cut-off. Any ratio greater than 1 is considered positive.

These results show that the OTC screening assay gave higher S/CO values than did the Coulter test. The disparity between the performance of the two tests was much greater with the antibody containing samples than the spiked (non-antibody containing) standards.

EXAMPLE 2

Acid Treatment of Samples

Immunoassays to detect the presence of the HIV-1 p24 antigen in human serum samples were performed using the Coulter screening assay and the Coulter immunoassay with acid dissociation pretreatment procedure.

A. Acid Dissociation Pretreatment Procedure.

This procedure was followed for each sample. 200 µl of the sample was added to a screw-topped tube. 200 µl of glycine reagent (1.5M glycine, pH 1.85, adjusted by concentrated HCl) was then added to the sample and the tube vortexed. The tube was capped and incubated at 37° C. for 1 hour. After incubation, 200 µl of Tris reagent buffer (1.5M Tris buffer, pH 9.0) was added to the tube, and the tube vortexed. The samples were then ready to be transferred to immunoassay microtiter plates.

B. HIV-1 p24 Immunoassay.

The Coulter screening assay was performed as described in Example 1 above, using untreated and acid pretreated samples, and only the acid pretreated sample was incubated overnight at 37° C. The results are shown in FIG. 2.

Figure 2:
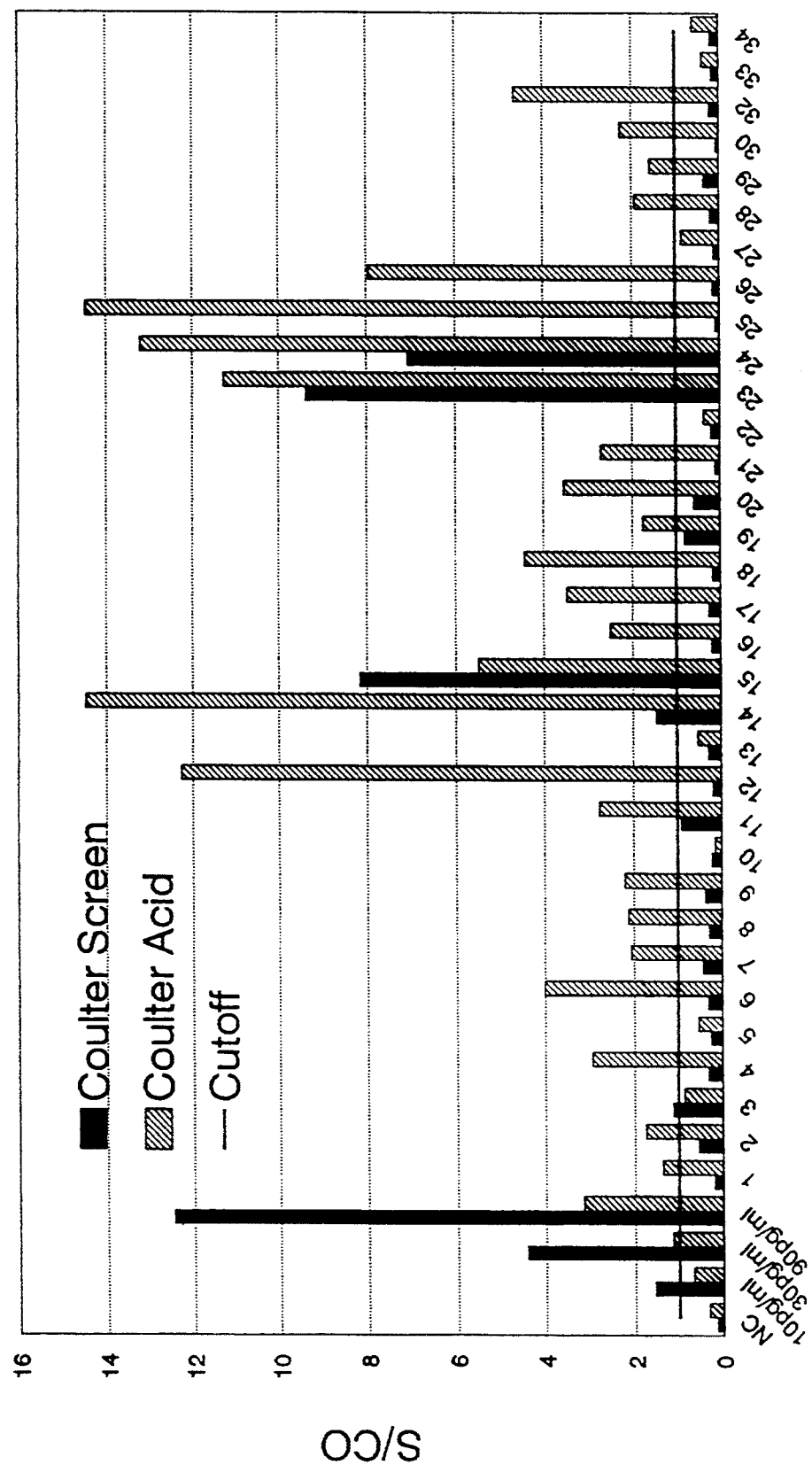
FIG. 2 is a graph of samples tested for HIV-1 p24 antigen using the Coulter Corporation screening immunoassay where one set of samples was not pretreated and another set of samples was pretreated by acid dissociation.

FIG. 2 is a graph comparing the results of the Coulter screening assay testing unpretreated samples and the results of the Coulter assay testing using acid dissociated pretreated samples. FIG. 2 shows that acid pretreatment of the antibody containing samples enhanced detection of complexed HIV p24 antigen. However, the acid treatment significantly comprised the immunoreactivity of the spiked standards and, to a lesser degree, samples 3 and 15.

EXAMPLE 3

Base Dissociation Pretreatment Procedure

This experiment was performed to compare the OTC screening assay for HIV-1 p24 antigen without a base dissociation treatment step to the OTC screening assay where the samples are treated by the base dissociation method.

The same controls, samples and standards were used as described in the previous examples.

The OTC screening assay was performed as described in Example 1 above.

Figure 3:
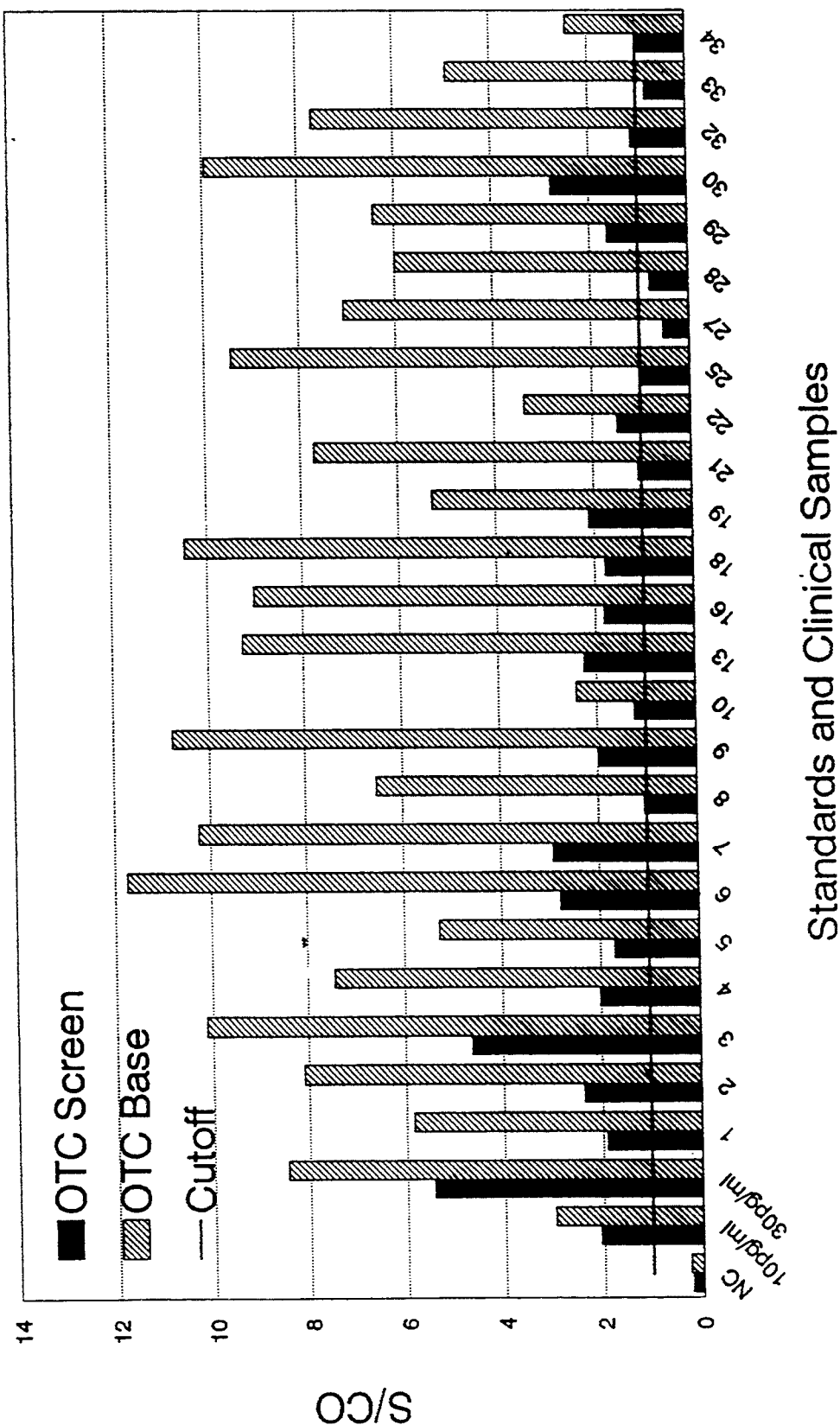
FIG. 3 is a graph of samples tested for HIV-1 p24 antigen using the Organon Teknika Corporation immunoassay where one set of samples was treated by base dissociation another was not.

The OTC screening assay with a base treatment step was performed the same as described in Example 1 above, with the following exceptions. The Disruption Buffer was replaced with 25 µl of Dissociation Reagent, which had the same composition as the Disruption Buffer, except that 1.5M ethanolamine and 2.5% Triton X-100 were added while the urea and saponin were removed, and the pH adjusted with HCl to 11.5. Also, incubation was changed to overnight at room temperature. The results are shown in FIG. 3. Any results with a S/CO greater than 14 were eliminated from the graph.

As shown in FIG. 3, the base dissociation procedure enhanced the ability of the OTC screening assay to detect HIV antigen in the presence of antibody. Unlike the Coulter acid dissociation procedure, the OTC base dissociation procedure did not compromise samples without antibodies, but actually enhanced the signals produced by the standards, when incubation was overnight, as compared to the one hour screening assay incubation. Additionally, comparing FIG. 3 to FIG. 2, it is seen that the OTC base dissociation procedure incubated in the microtiter well overnight detected antigen in every sample, whereas seven samples were not detected by the combination of both Coulter's screening and acid dissociation assays.

EXAMPLE 4

Dissociation Methods Compared

The Coulter acid dissociation assay was compared to the OTC base dissociation assay performed with three hour and overnight incubation. All samples, controls and standards are as described above. The Coulter acid dissociation assay was performed as described in Example 2. The OTC base dissociation assays were performed as described in Example 3, except that in one assay the microtiter plates were incubated for three hours at 37° C. and in overnight at room temperature. In the three hour assay, the Dissociation Reagent had a pH of 11, and in the overnight assay, it had a pH of 11.5. The results are shown in FIG. 4.

In both the standards and the samples, the OTC tests detected greater amounts of antigen than did the Coulter test assay. In general, S/CO values for the overnight OTC immunoassay were higher than those seen for the three hour test. According to this Figure, it appears that with samples 14, 23 and 24, the overnight OTC assay produced lower signals than did the three hour assay. However, signals from each of these samples were off the scale, and because of slightly different negative control background signals the maximum S/CO values generated by each assay was slightly different, making the overnight assay seem artificially lower. The Coulter assay produced a higher signal with sample 25.

Figure 4:
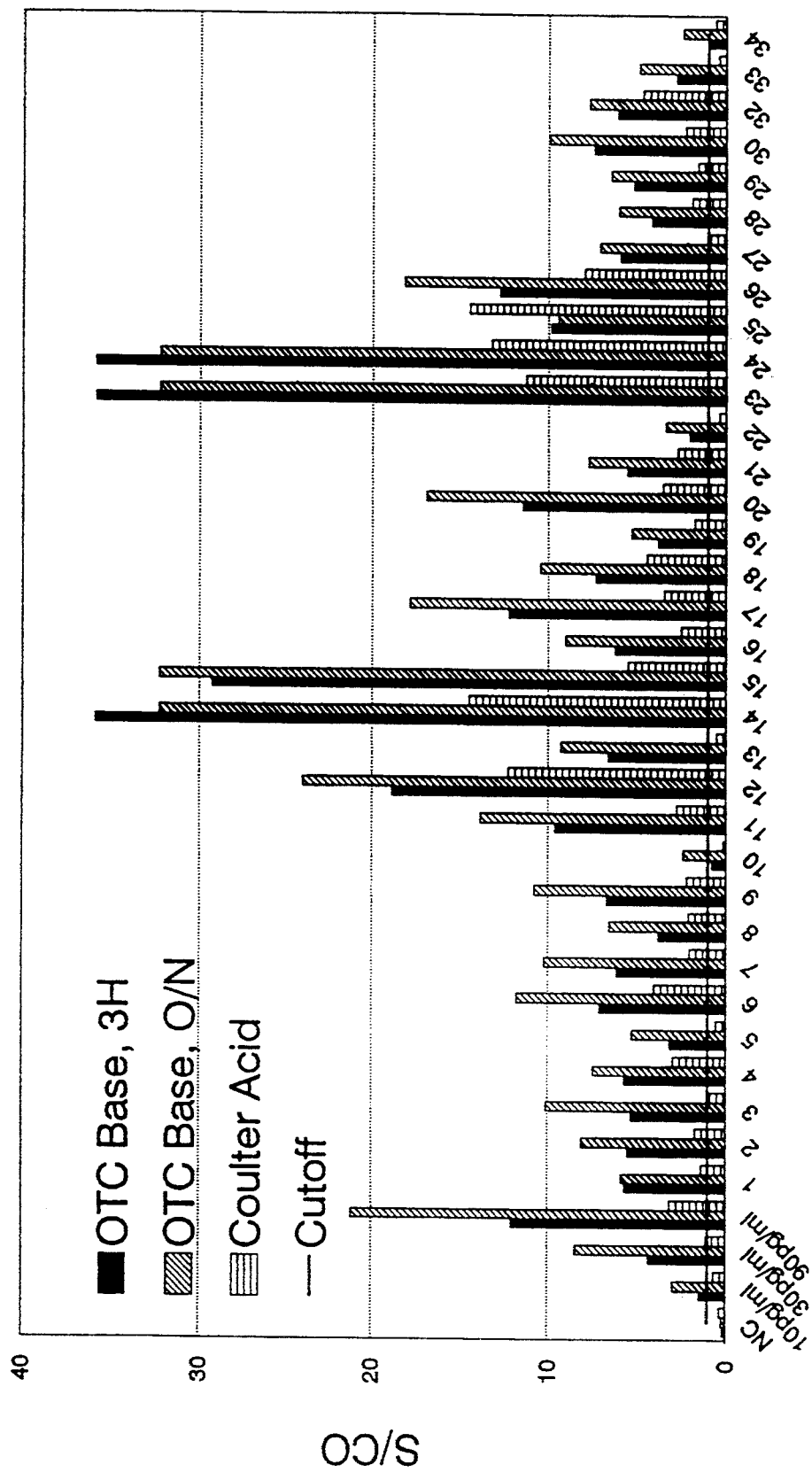
FIG. 4 is a graph comparing the Coulter Corporation acid dissociation immunoassay to the Organon Teknika Corporation base dissociation immunoassay.
Figure 5:
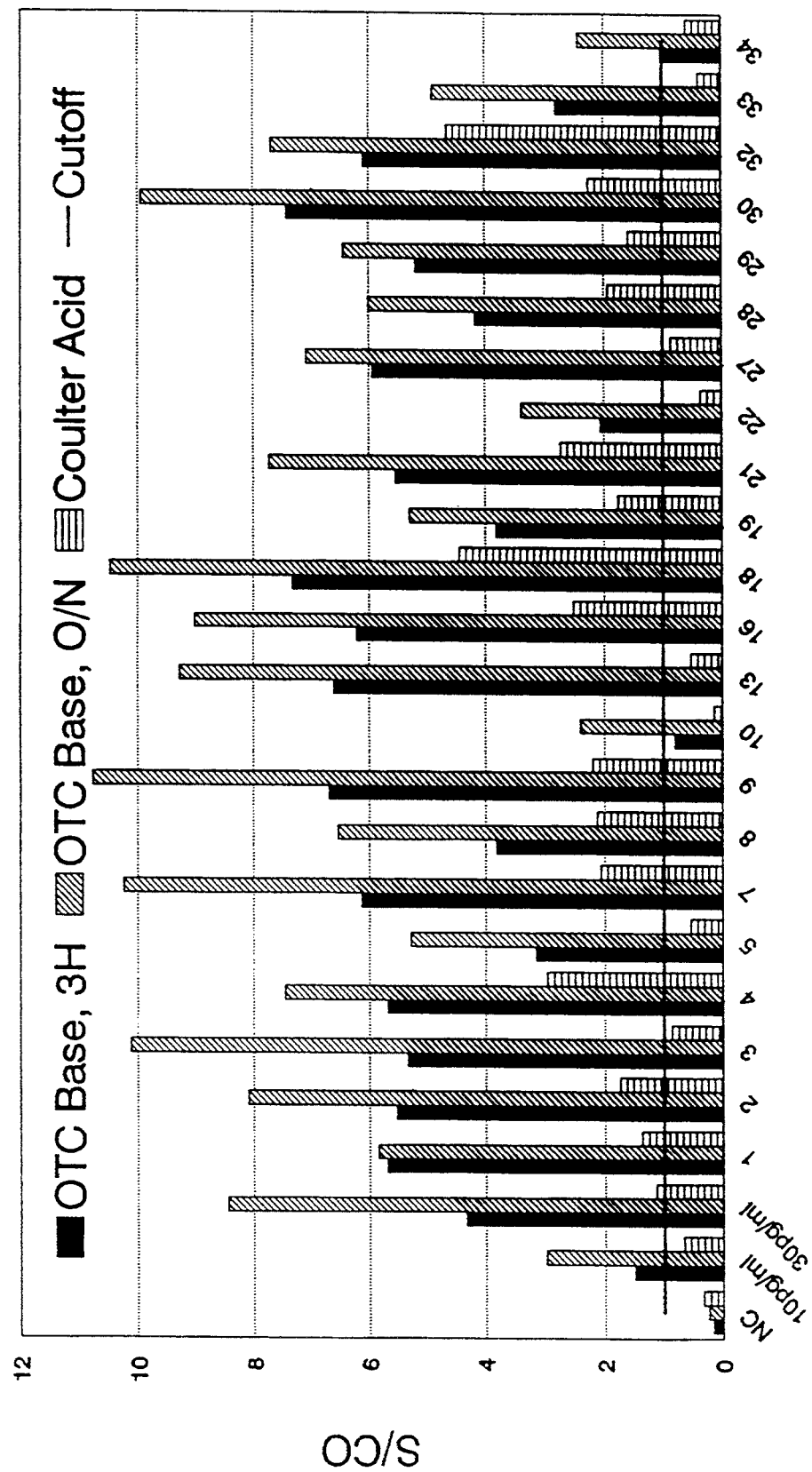
FIG. 5 is a graph as is the same as FIG. 4, except that all values above the S/CO of 12 have been removed.

FIG. 5 contains the same data as seen in FIG. 4, except that all samples with a S/CO value greater than 12 were eliminated. With the cut-off for a positive result being a S/CO of 1, the Coulter assay missed eight of the samples.

EXAMPLE 5

Comparison of Acid and Base Dissociation Methods in OTC Immunoassays

These assays compared the screening assay and acid and base dissociation methods when detecting HIV-1 p24 antigen using the OTC immunoassay.

Standards, samples and controls used were the same as those described in the examples above.

One assays using the base dissociation procedure as described in Example 3 was performed on the samples with a Dissociation Reagent at pH 11.5 and an overnight incubation at room temperature.

The acid dissociation pretreatment procedure was performed as described in Example 2, and once the samples were neutralized, the test samples were transferred to the Vironostika ® HIV-1 Antigen Microelisa System kit screening assay microtiter plates and acid treated samples were incubated overnight at 37° C.

The immunoassay was performed for all three sets of samples as described in Example 1 above.

Figure 6:
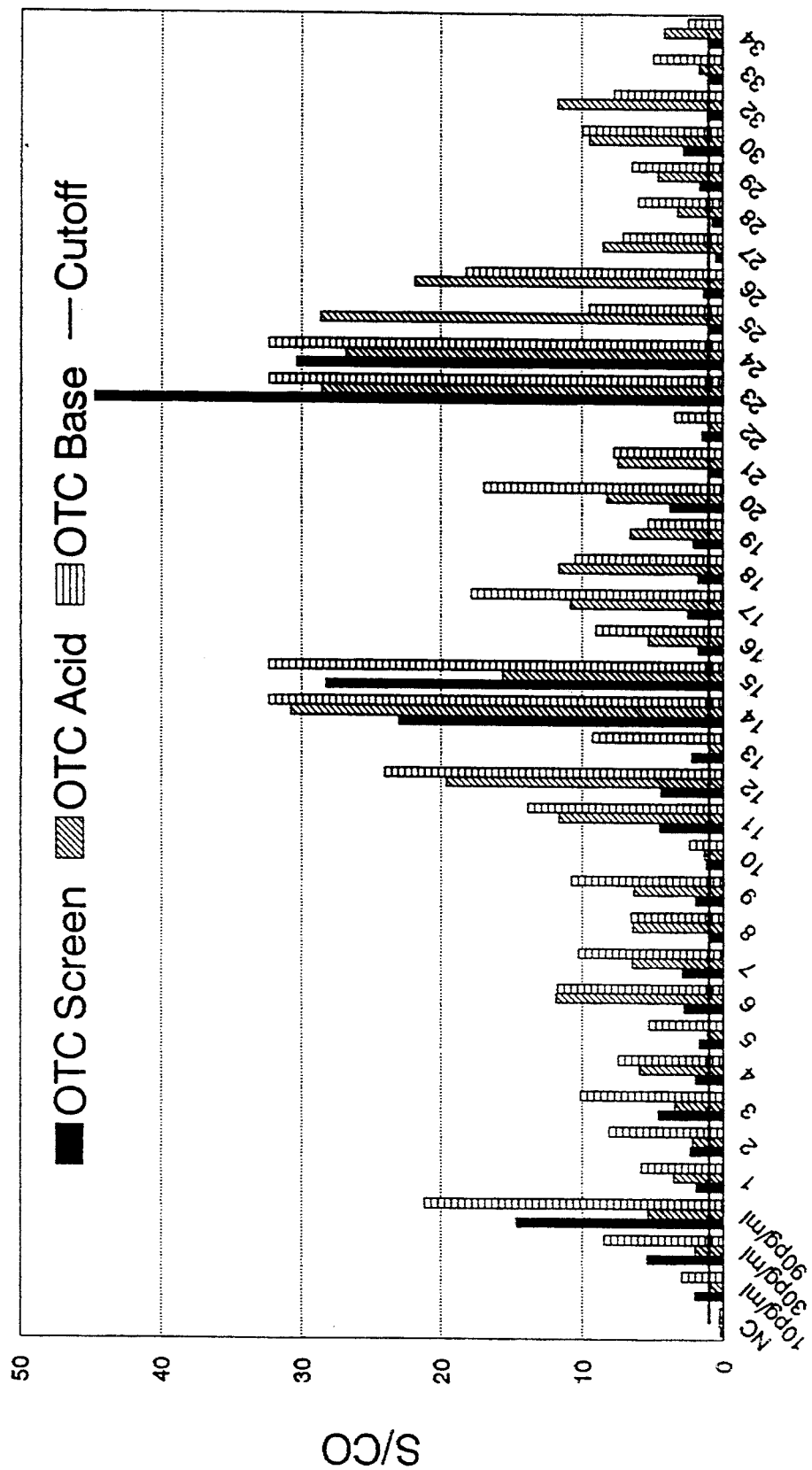
FIGS. 6 and 7 are graphs comparing the screening assay, an acid dissociation pretreatment procedure and a base dissociation procedure on detection of HIV-1 p24 antigen.
Figure 7:
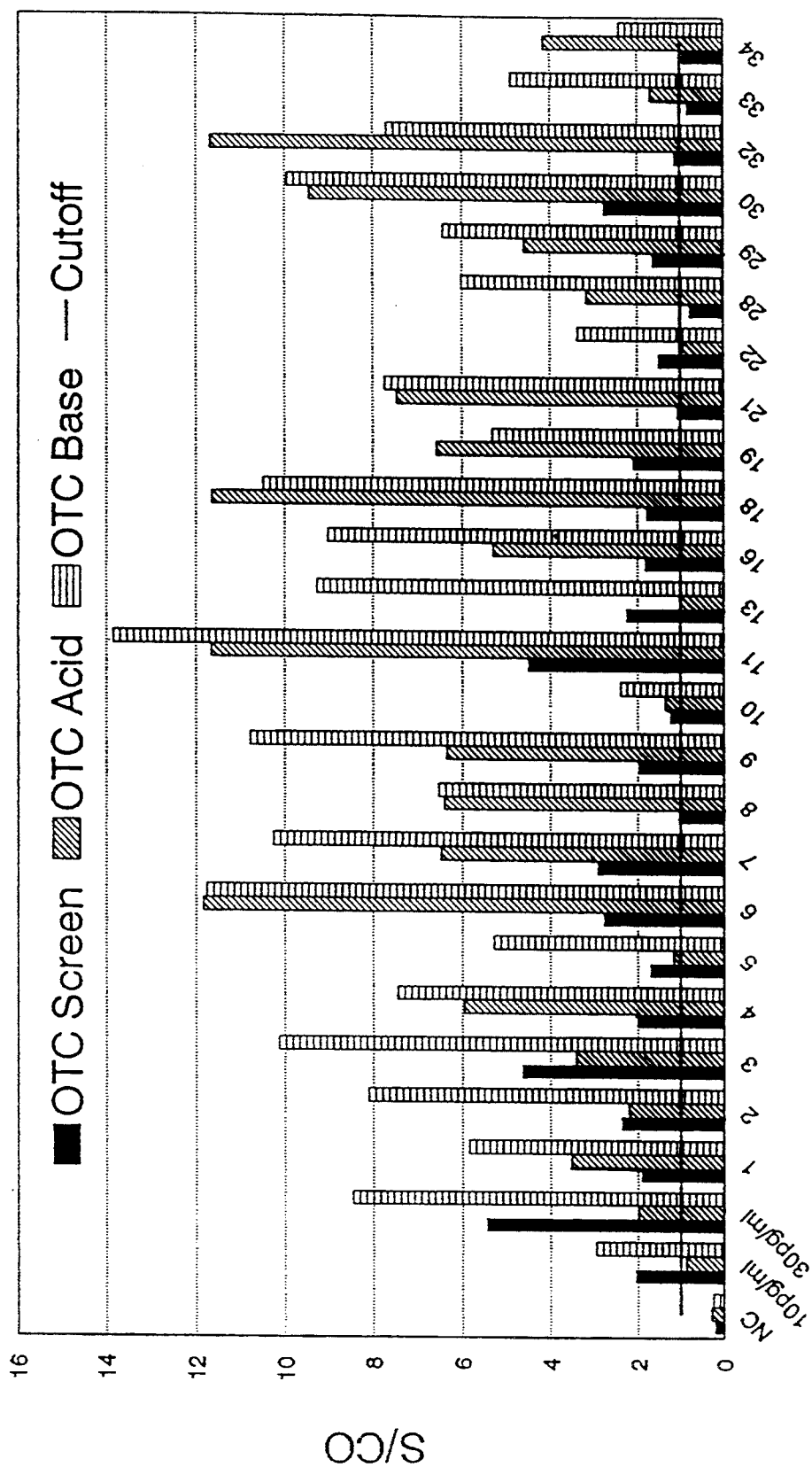

The results of the immunoassays are shown in FIGS. 6 and 7. The screening format detected twenty-five positive samples and eight samples with elevated signals, but below the cut-off of S/CO of 1. The overnight acid dissociation method detected 31 out of 33 samples as positive. The two negative results were shown to be positive by the normal screening assay. The overnight base dissociation assay detected all 33 samples. Additionally, the overnight base dissociation assay was 4–5 times more sensitive on non-antibody containing samples (the standards) than the overnight acid dissociation method.

EXAMPLE 6

Determination of Optimum pH

The following experiments were performed to determine the optimal pH range for the base dissociation assay. The samples were analyzed using the Vironostika ® HIV-1 Antigen Microelisa System kit with the changes noted below.

The samples to be tested for the first assay were HIV-1 p24 antigen lysate diluted $1 \times 10^5$ into normal human serum, the same lysate diluted $1 \times 10^4$ mixed with $1 \times 10^3$ anti-p24 antibody containing serum and the same lysate diluted $1 \times 10^4$ mixed with $1 \times 10^4$ anti-p24 antibody containing serum.

The assays were performed as described in Example 1, except that after the sample and Disruption Buffer were added to the microtiter plate well, 25 µl of Base Buffer was added. Base Buffer was a solution of 0.6M CAPS (3-[cyclohexylamino]-1-propane-sulfonic acid) and 0.6M ethanolamine, adjusted to pH with NaOH or HCl. Each of the test samples was run at a pH of 9, 9.5, 10, 10.5 and 11, and also at pH 7.3 where no Base Buffer was added, but instead 25 µl of phosphate buffered saline, to have the same final volume in the test well. The microtiter plates were incubated for 2 hours at 37° C. instead of one hour. The results are shown in FIG. 8.

Figure 8:
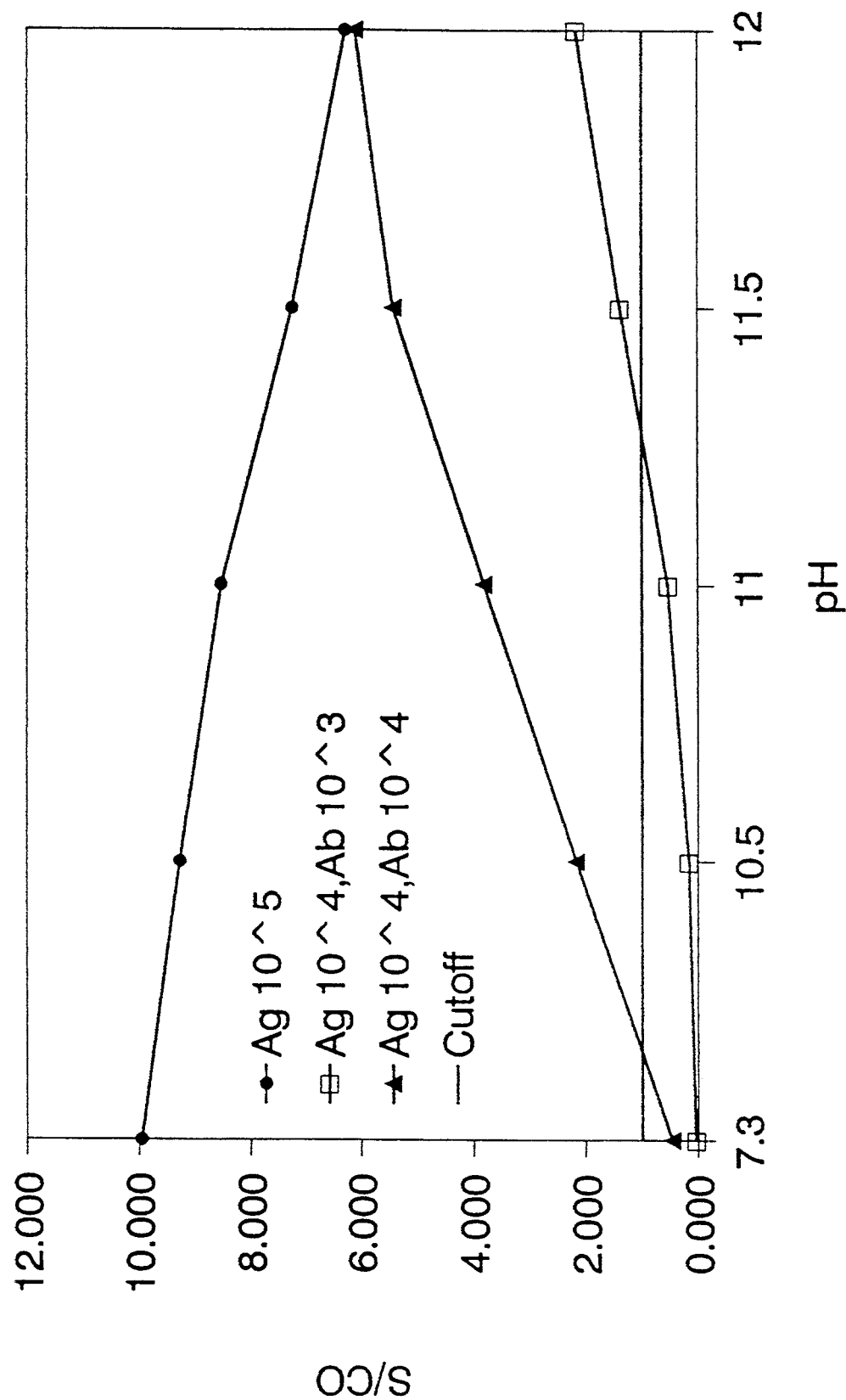
FIG. 8 is a graph of pH versus S/CO for standardized samples base dissociated at various pH values.

FIG. 8 shows that detectability of immunocomplexed antigen is enhanced as the pH increased from 7.3 and particularly from pH 10 through pH 12.

EXAMPLE 7

Effect of Incubation on Base Dissociation Method

This experiment was performed in order to determine if a longer incubation time would improve the sensitivity of the immunoassay after samples had been pretreated using the base dissociation method.

The Vironostika ® test kit and procedure as described in Example 1 above were used on six clinical samples and a spiked sample containing 10 pg/ml of p24 antigen, except that the Disruption Buffer was replaced by the Base Dissociation Reagent as described in Example 3 above with the pH adjusted to 11, 11.5, and 12. Additionally, sample incubation was either two hours at 37° C. or overnight at room temperature. The results are seen in FIG. 9.

Figure 9:
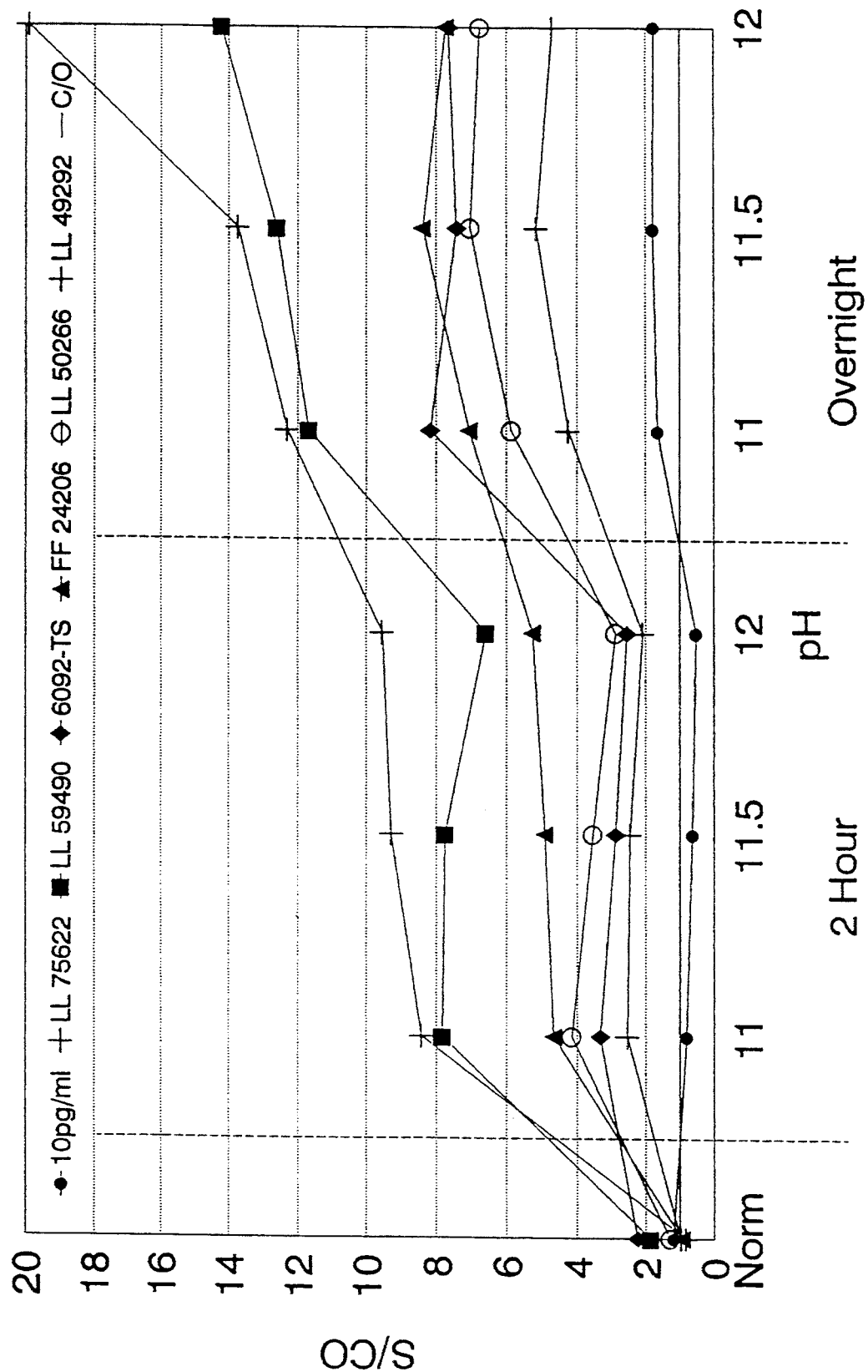
FIG. 9 is the same as FIG. 8, additionally comparing the effect of two incubation periods.

FIG. 9 shows that although all immunocomplexed samples showed enhanced detectability even at two hours incubation, the noncomplexed sample (the 10 pg/ml sample) showed decreased detectability. However, after overnight incubation, all samples, including the noncomplexed sample, showed enhanced detectability.

These examples show that the base dissociation method is an easier, less complicated assay than the acid dissociation pretreatment method, as it is performed in the microtiter well and needs no neutralization step prior to an immunoassay being performed. It is more sensitive than many acid dissociation methods in both detecting free antigen and antigen freed from its antibody immunocomplex by the dissociation step and in detecting the amount of antigen in the samples.

I claim:

1. A method to enhance the detection of antigen in a sample by forming an immunocomplex of the antigen with a capture antibody, wherein in the sample the antigen is complexed with an antibody as an immunocomplex, comprising adding a reagent having a basic pH to the sample to adjust the pH to a pH greater than about 8.0, thereby dissociating the immunocomplex and releasing antigen; contacting the sample having a pH of greater than about 8.0 with a capture antibody bound to a solid substrate, whereby new immunocomplexes are formed; and detecting the presence or absence of the new immunocomplexes, thereby determining the presence or absence of said antigen.

2. A method according to claim 1, wherein the sample is adjusted to a pH in the range of from about 9.0 to about 14.0.

3. A method according to claim 2, wherein the pH range is from about 10.0 to about 12.0.

4. A method according to claim 1, wherein the antigen is selected from the group consisting of peptides, proteins and haptens.

5. A method according to claim 1, where the antigen is selected from the group consisting of Human Immunodeficiency Virus type 1 (HIV-1) p24 antigen, Human Immunodeficiency Virus type 1 (HIV-2) p 24 antigen, antigen from Human T-Cell Lymphtrophic Virus type 1 (HTLV-I), antigen from HTLV-2, and antigen from Hepatitis C Virus.

6. A method according to claim 1, wherein the antigen is human immunodeficiency virus type 1 p24 antigen.

7. A method according to claim 1, wherein the antigen is human immunodeficiency virus type 2 p24 antigen.

8. A method according to claim 1, wherein the sample is selected from the group consisting of plasma, serum, urine and cerebral spinal fluid.

9. A method according to claim 1, wherein the basic solution is a composition of a salt, a buffer with a pKa at a basic pH, and a surfactant selected from the group consisting of nonionics, anionics, cationics and zwitterionics.

10. A method according to claim 9, wherein the salt is NaCl, the buffer is ethanolamine and the surfactant is Triton X-100.

11. A method according to claim 10, wherein the NaCl has a concentration of 0 to about 3M, the ethanolamine has a concentration of about 0.01M to about 10M, and the Triton X-100 has a concentration from 0% to about 10%.

12. A method according to claim 1, wherein the solid substrate is selected from a group consisting of microtiter plate wells, beads, strips, test tubes, capillary tubes, gold sol, red blood cells and latex particles and wherein dissociating the immunocomplex in the sample and forming immunocomplexes with the capture antibody occur concurrently.

* * * * *